United States Patent [19]

Frankenberger

[11] 4,050,823
[45] Sept. 27, 1977

[54] APPARATUS FOR CONTINUOUSLY MEASURING THE $CO_2$ CONTENT IN BREATHING GASES

[75] Inventor: Horst Frankenberger, Bad Schwartau, Germany

[73] Assignee: Dragerwerk Aktiengesellschaft, Lubeck, Germany

[21] Appl. No.: 707,503

[22] Filed: July 22, 1976

Related U.S. Application Data

[62] Division of Ser. No. 609,564, Sept. 2, 1975, Pat. No. 4,011,859.

[30] Foreign Application Priority Data

Sept. 5, 1974 Germany .............................. 2442589

[51] Int. Cl.$^2$ ................................................ G01J 3/50
[52] U.S. Cl. .................................... 356/186; 250/343; 356/51; 356/201
[58] Field of Search ................. 356/51, 201, 205, 246, 356/184, 181, 186; 250/343, 573, 574, 576; 350/61; 128/2 C, 2 L, 2 R, 2.07

[56] References Cited

U.S. PATENT DOCUMENTS

3,935,463    1/1976    Jacobsen .......................... 356/51 X

FOREIGN PATENT DOCUMENTS

902,732    8/1962    United Kingdom ................. 356/205

*Primary Examiner*—F. L. Evans
*Attorney, Agent, or Firm*—McGlew and Tuttle

[57] ABSTRACT

A method of continuously measuring the $CO_2$ content in breathing gases during inspiration and exhalation phases of breathing using a luminous source to pass infrared light rays through an interference filter accorded to $CO_2$ and a conduit of the gas to a photodetector, comprises passing the breathing gas developed during the breathing phases through the conduit to influence the photodetector to transmit a measured value signal in accordance with the $CO_2$ content, directing the signal to a breathing air phase recognition unit, storing the maxima and the minima of the measured value signals in each breathing phase in a maximum storage and a minimum storage, dividing the stored values under the control of the recognition unit and directing the values to a computation unit to indicate the logarithm of the values so as to give an indication of the variations of the $CO_2$ content. The indicated value is then directed to an indicating unit to show the value of the $CO_2$. The apparatus includes a tubular cell or conduit comprising a measuring cell which is arranged centrally between a luminous source and an interference filter accorded to $CO_2$ on one side and a photodetector on the other side thereof. A measuring cell tube is mounted on a stable support which is adapted to be warmed up during operation. The system includes a light modulator between the luminous source and the interference filter and a lens system for directing the light through the measuring cell and through the photodetector.

3 Claims, 5 Drawing Figures

APPARATUS FOR CONTINUOUSLY MEASURING THE CO₂ CONTENT IN BREATHING GASES

This is a division of application Ser. No. 609,564, filed Sept. 2, 1975, now U.S. Pat. No. 4,011,859.

FIELD AND BACKGROUND OF THE INVENTION

This invention relates in general to a method and apparatus for measuring gases and, in particular, to a new and useful method and apparatus for continuously measuring the CO₂ content in breathing gases.

DESCRIPTION OF THE PRIOR ART

Various method and devices which operate on the principle of infrared absorption for continuously measuring the concentration of individual components in gases and vapors are known. They are used, for example, for controlling the processes in chemical plants for the environmental control of air and also in medicine. The measuring effect of the infrared absorption devices is based on the specific absorption of the radiation of heteroatomic gases in the infrared spectral region. The radiation is absorbed at definite frequencies associated with the natural oscillation of the molecules. With the exception of the monoatomic rare gases and the diatomic element gases, such as oxygen and hydrogen, any gases possesses an absorption spectrum in its infrared region which is composed of individual absorption bands and is specific for the respective gas.

In the known devices, the absorption takes place in a cell which is integrated within the measuring instrument and through which the gas sample is conducted. For the intensity $I$ of an undulatory radiation subjected to absorption and having passed through a medium layer with a thickness $l$, Lambert-Beer's law is applicable according to which $$I = I_o \cdot e^{-k \cdot l \cdot c}$$

where $I_o$ is the light intensity at its entrance into the medium
$k$ is the extinction coefficient
$l$ is the path within the cell
$c$ is the concentration of the gas All of the known gas analysis devices operating on the infrared absorption principle use the radiation absorption in the infrared spectral region, which is specific for the gas to be measured. The following operational methods are used:

Two-channel method

The equiphase modulated radiation emitted by two incandescent coils passed in parallel beams through a reference chamber and a measuring chamber and reaches the receiving chamber. The latter is subdivided into two compartments by means of a diaphragm capacitor. Both compartments are filled with the gas to be measured. The measuring chamber contains the gas to be measured while the reference chamber is filled with an inert gas, such as nitrogen, which does not absorb any radiation. Both beams of radiation, through the reference chamber, as well as through the measuring chamber, are periodically, and in phase, interrupted by means of a rotating screening wheel.

As soon as, due to the presence of the gas to be measured, the beam transmitted through the measuring chamber is partly absorbed, the differential signal thereby produced causes periodic pressure and temperature variations in the receiving chamber. These variations generate capacitance variations in the diaphragm capacitor which are a function of the concentration and may be made perceptible in a gas indicator.

Single-channel method

The radiation which is emitted by an incandescent coil and modulated in opposite phase by a rotating screening wheel passes in parallel through a reference chamber and a measuring chamber which are provided in a two-part cell, and reaches the receiving chamber. The receiving chamber is subdivided into two compartments and filled with the gas to be measured. Both compartments act on a diaphragm capacitor. As soon as, due to the presence of the gas to be measured, the radiation is partly absorbed in the measuring chamber, the differential signal thereby produced causes pressure and temperature variations. These variations generate capacitance variations in the diaphragm capacitor which are a function of the concentration and may be made visible in a gas indicator.

Single-channel method with a reference receiver

The radiation of a Hg-vapor lamp beamed by means of a quartz condenser passes through an interference filter to a beam splitter in which one half of the light is deviated to a reference receiver. The other half of the beam passes through the measuring cell. In a program-controlled manner, the measuring cell is alternately filled with an inert gas corresponding to the zero point, and the gas sample to be measured. Each time, a two-beam photometer compares the two values, the zero point and the measured value with the value supplied from the reference receiver. While inert gas flows through the measuring cell, a motor-driven potentiometer can bring the measuring bridge into balanced state. The scavenging and balancing intervals are adjustable and are chosen according to the contamination of the cell to be expected (periodical "Wasser, Luft and Betrieb" 8, 1974).

Another known infrared-absorption measuring device for measuring the CO₂ content in the expiration air operates without a reference gas in the beam path of the luminous source which, in this case, is a NiCr wire coil. Two paths of rays are provided in the device, which differ from each other by the interposition of a reference filter and an analytical filter, resectively. In the order of transmission after the luminous source, the rays pass the measuring cell, then, according to the switching position, either the reference filter or the analytical filter, and subsequently, a broad-band filter covering the wavelengths of both the reference filter and the analytical filter, and a photodetector. The measuring device also comprises further well-known equipment for amplifying the measuring signals coming from the photodetector, the synchronizing switching mechanism, etc.

The measuring cell is mounted is a bypass of the expiration air. The bypass current of the expiration air which is moved by a small transistorized pump flows through small passages into the measuring cell to pass through the entire cross-sectional area thereof. Similar passages are provided at the outlet side. With this measuring cell, the measuring device is capable of testing up to forty breathing strokes per minute having a rate of flow of 0.6 l/min.

The wave length of the reference filter is approximately 5 μm, that of the analytic filter about 4.26 μm.

The broadband filter comprising a lead-tellurium layer and a glass layer prevents the passage of rays having wavelengths shorter than 3.75 μm and longer than 5 μm.

The wavelength of the reference filter has been chosen so as to prevent an absorption in the gas sample, thus in the expiration air, even in the presence of $CO_2$. The wavelength of the analytic filter, however, largely corresponds to the absorption band of the substance to be measured. The resulting difference of the measuring signal in the photodetector is the measured value.

In practice, the time necessary for each of the measurements is largely determined by the intake and exhaustion of the respiration air, along with the scavenging of the cell. The scavenging of the cell is a problem. This is why the narrow passages distributed over the entire cross-sectional area are necessary. A uniform scavenging of the cell, however, cam be obtained only if all the passages are clean (D. W. HILL and R. N. STONE, J. SCI. INSTRUM, 1964, Vol. 4J).

The methods mentioned in the foregoing, using the infrared absroption for measuring a gas, are disadvantageous for a determination of the $CO_2$ content in breathing gases. The measuring cells with the measuring equipment are too big and heavy to permit a mounting directly in the respiration circuit. In addition, even with the use of the largest cells, the rate of flow of the gas to be measured does not exceed about 60 1/h. With such a small sample quantity, they cannot be mounted directly in the breathing-gas stream. Consequently, they must be supplied through a bypass. The time lag of the scavenging and refilling of the cell with the breathing gas to be measured caused by the bypass makes a direct control of the respiration phases almost impossible. With the mentioned measuring methods, the variations of pressure and temperature in the breathing-air stream lead to losses of sensitivity in the measured value. The taking of a gas sample from the respiration circuit and its supply through a bypass requires a costly instrumentation if a disturbance of the result of measurement by other influencing quantities, like gas flow, elasticity of the lungs, stroke volume, etc., is to be prevented.

Reference gases with the necessary flow direction arrangements make the measuring devices complicated and, they are only an auxiliary means for detecting or compensating the sensitivity variations and zero-point displacements caused by the contamination of the cells and the aging of component parts, such as emitters, receivers, etc.

SUMMARY OF THE INVENTION

The present invention provides a measuring method for a delay-free determination of the continuous $CO_2$ content of breathing gases at the end of the expiration phase, in which unnoticed measuring errors, for example, due to a contamination of the cell or aging of component parts, are securely eliminated.

In accordance with the invention, the measured values of a measuring cell which is placed in the breathing-air stream, are processed in a signal processing unit which is controlled by a breathing-air phase recognition unit, the respective maxima and minima of the measured values of each breathing phase are stored in a maximum-value storage and a minimum-value storage, these values, controlled by the breathing-air phase recognition unit, are divided and the logarithm is taken thereof in a computation unit and, since $$In \frac{I \, \text{expir.}}{I \, \text{inspir.}} \stackrel{\triangle}{=} c_{CO_2},$$

the $CO_2$ content at the end of the expiration phase is indicated in an indicating unit.

According to a development of the invention, the continuously measured value of the $CO_2$ content in each breathing phase, after division by the minimum value from the minimum-value storage and logarithmation in the computing unit, is applied to the output terminal. The particular advantage of this method is that no reference gas and no movable component parts are needed. By placing the measuring cell directly in the breathing-air stream and, thus, using the entire breathing gas volume as a sample, a delay-free, accurate and, because it is independent of additional conditions of a bypass, representative and reproducible measurement is ensured. Futher substantial advantages of this method are the elimination of the influence of other gas components of the breathing gas and the avoidance of the critical problem of a zero point.

The gas measuring device for carrying out the gas measuring method comprises a replaceable measuring-cell tube which is received in a mounting designed as a stable support adapted to be warmed up and accommodating a luminous source, a system of lenses, an interference filter and a photodetector.

The advantages obtained with this embodiment are to be seen in that due to the possibility of providing small dimensions, the device can easily be placed in the breathing-air stream close to the mouthpiece, without annoying the patient. The measuring-cell tube is easily replaceable and, therefore, complies with the requirement for sterility imperative in the medical art. Upon removal, the tube may either be sterilized or replaced by another. The measuring-cell tube is a simple structure comprising no further equipment necessary for its function and, consequently, it is inexpensive.

The device for carrying out the gas measuring method further comprises a light modulator which is provided between the luminous source and the interference filter. This is advantageous in cases where light-transmitting connecting tubes are used for avoiding stray light effects.

Accordingly, it is an object of the invention to provide an improved method of continuously measuring the $CO_2$ content in breathing gases during the inspiration and exhalation phases of breathing and using a luminous source to pass infrared light rays through an interference filter which is accorded to $CO_2$ and through a conduit of the gas to a photodetector, comprising continuously passing the breathing gas developed during the breathing phases through the conduit to influence the photodetector to transmit a measured value signal in accordance with the $CO_2$ content, directing the signal to a breathing air phase recognition unit, storing the maxima and the minima of the measured-value signals in each breathing phase in a maximum storage and a minimum storage, dividing the stored values under the control of the recognition unit and directing the values to a computation unit to indicate the logarithm of the values so as to give an indication of the variations of $CO_2$.

A further object of the invention is to provide an apparatus for measuring $CO_2$ content in breathing gases which comprises a tubular measuring cell made of a light transmissive material through which the breathing gases are passed and means for mounting said cell between a light source and an interference filter on one side and a photodetector on the other side, said mounting being of a material which is capable of being warmed up and further including a lens system for controlling the direction of the light from the light source through the measuring cell tube to the photodetector.

A further object of the invention is to provide a device for measuring the $CO_2$ content of breathing gases which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there is illustrated a preferred embodiment of the invention.

DESCRIPTION OF THE PREFERRED EMBODIMENT

Figure 1:
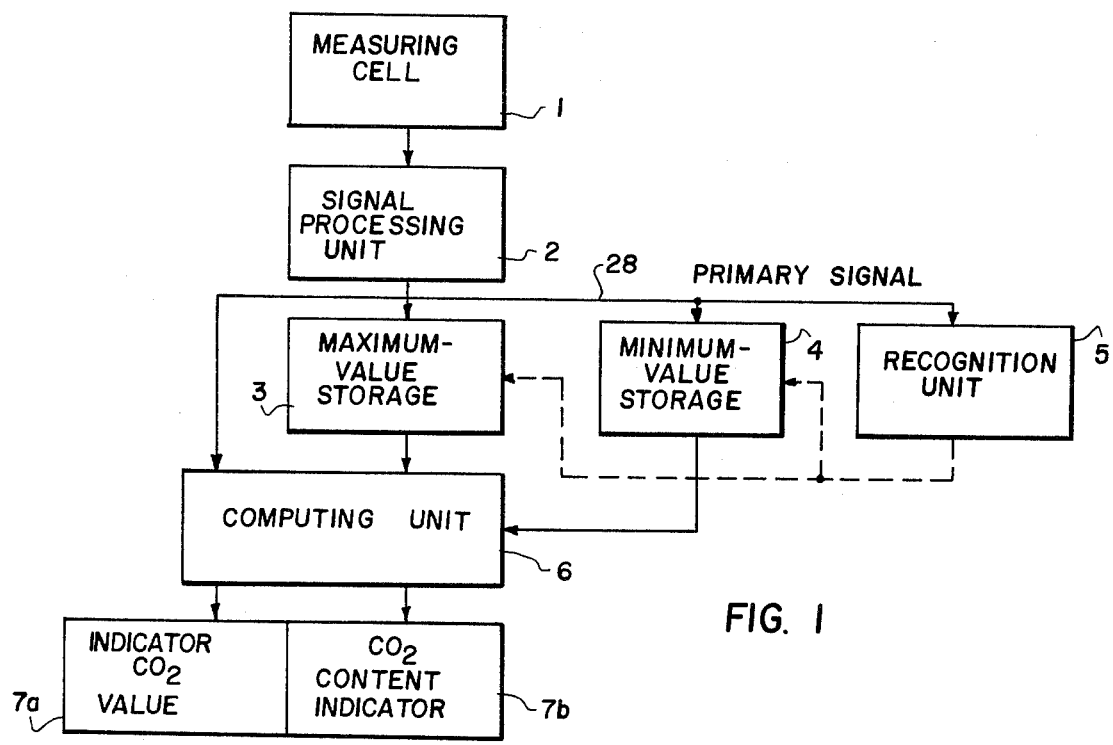
FIG. 1 is a block diagram of the gas measuring method of the invention.
Figure 5:
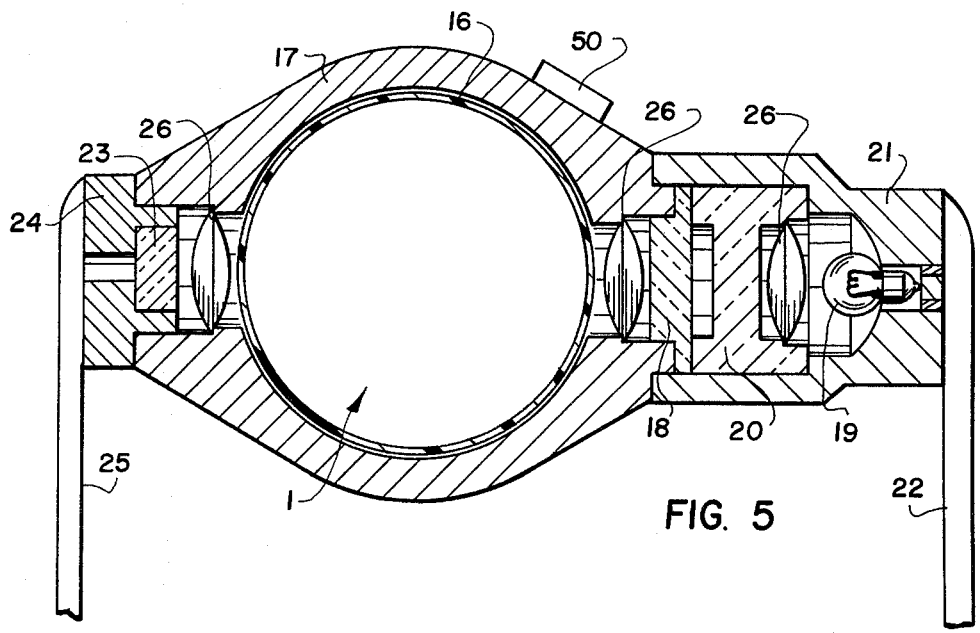
FIG. 5 is a cross-sectional view of a measuring cell constructed in accordance with the invention.

Referring to the drawings in particular, the device for measuring the $CO_2$ content in a breathing gas, comprises a measuring cell, generally designated 1, which includes a tubular measuring member made of a translucent material which is received in a mounting 17 which may be disposed close to a patient's mouth and between a mouthpiece for the patient and a well-known Y-piece connection which is provided in the respiration line. The measuring-cell tube 16 is made of a suitable infrared transmitting plastic and it is intended for a single use. In order to prevent condensation of water droplets on the inside of measuring cell tube 16, the tube is heated through an appropriately designed heater 50 which is engaged on the mounting 17 or embedded therein in order to effect the heating thereof, such as by electrical resistance heating. Mounting 17 is preferably a concentric tube made of a resistance material having a positive temperature coefficient. A positive temperature coefficient material changes its resistance with the increasing temperature so that at temperatures below the switching temperature, the resistance increases only slightly with the temperature. Upon exceeding the switching temperature, however, the temperature dependence of the resistance rises by a multiple. Thus, with the positive temperature coefficient material resistance connected to a constant voltage source, the temperature is kept at a constant level in a reliable and simple manner.

In the preferred form, the mounting 17 comprises a tubular member which may be heated up to approximately 40° C which is provided with openings or slots through which an infrared radiating light ray may pass. The mounting is provided with a cavity for mounting a luminous source 19 providing an infrared radiating source. A light modulator 20 is aligned with the light source 19 along with an interference filter 18 (about 4.25 μm), and a photodetector 23 which is responsive to infrared light so that the emitted light, prior to its incidence on the photodetector 23, must pass through the interference filter 18 and the measuring cell tube 16. To direct the light through tube 16 in an optimum manner, the rays are beamed or controlled by means of a lens system which includes preferably several lenses such as the lens 26.

The equipment of the measuring cell 1 is completed by current supply lines 22, a holder 21 for the luminous light source 19, a holder 24 for the photodetector 23 along with signal lines 25 from the photodetector to a further processing device for processing the signals, such as indicated in FIG. 1 by the numeral 2.

A variation of the light intensity results in a directly proportional variation of the resistance of photodetector 23 which is responsive thereto. In accordance with Lambert-Beer's law, however, the functional relationship between the light intensity and the $CO_2$ concentration in the measuring cell is $$I = I_o \cdot e^{-K \cdot l \cdot c}.$$

Thus by measuring the resistance of the photodetector, an exponential measure of the $CO_2$ concentration is obtained as the measuring signal. This may be done, for example, by means of a resistance bridge, but other circuits may also be usable.

Figure 2:
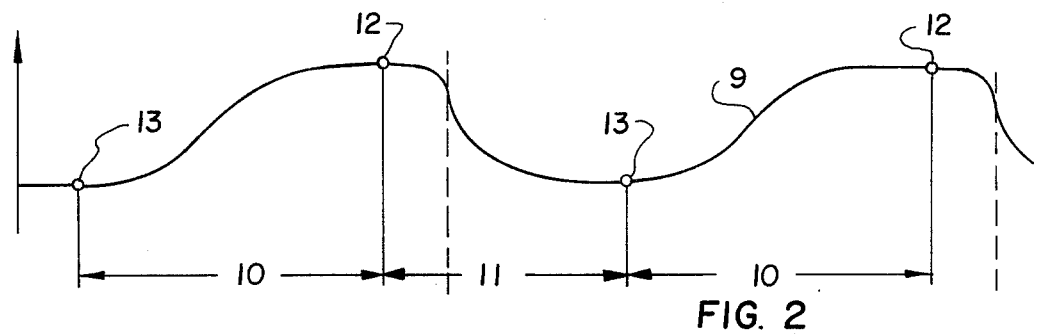
FIG. 2 is a curve indicating variations of the primary signal during the breathing phases.

As air is inhaled and exhaled in the breathing phases through the measuring cell tube 16, the measuring signal, after conversion in the signal processing unit 2, takes a typical shape as indicated at 9 in FIG. 2. Signal processing unit 2 transforms the response of the photodetector 23 to the light intensity variation into a suitably strong primary signal 28.

During the inspiration phase 11, no $CO_2$ is present and the light absorption is at its minimum 13, as shown in FIG. 2. During the expiration phase 10, the $CO_2$ concentration increases continuously to reach its maximum at the end of the expiration. After a short delay caused by the necessary scavenging of the measuring cell tube, the inflection point of the curve between expiration and inspiration is followed by a steep drop of the measuring signal.

Figure 3:
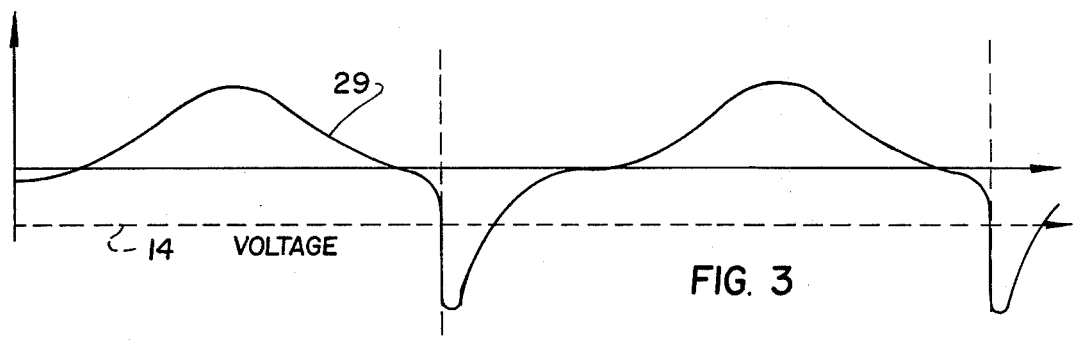
FIG. 3 is a curve showing the variation of the control signal.
Figure 4:
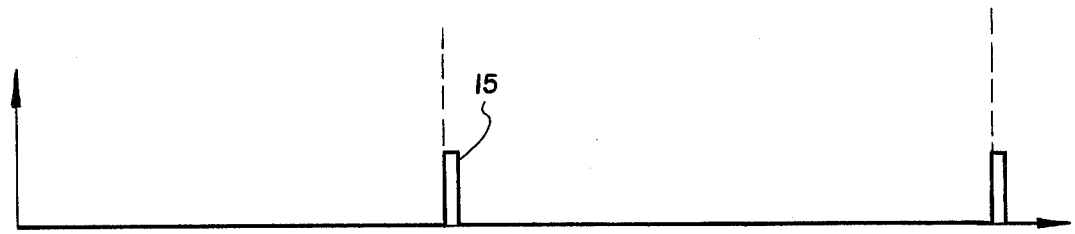
FIG. 4 is a diagram showing a control signal as a pulse signal.

This deep drop of the measuring signal is used by the breathing phase recognition unit 5 to produce a signal for the controlling of the maximum-value storage 3 and a minimum-value storage 4, as shown in FIG. 1. The breathing air recognition unit 5 comprises a differentiating unit forming the derivative 29, as shown in FIG. 3, of the primary signal with respect to the time. By superposing a voltage 14, a clear intersection between the abscissa and the derivative is obtained which is used for producing a pulse signal 15, as shown in FIG. 4, by means of a comparator and a following monostable multivibrator.

With the pulse signal 15, maximum-value storage 3 and minimum-value storage 4 are controlled so that, during a breathing cycle, that is, inspiration and expiration, these storages determine the maximum 12 and the minimum 13 values, respectively, store them and, as soon as the expiration is terminated, forward them to a computing unit 6. The circuitry of suitable maximum-value 3 and minimum-value 4 storages belongs to the prior art.

In computing unit 6, the quotient of the primary signal 9 by the stored value of the minimum-value storage 4 is continuously formed in time. Subsequently, the logarithm is taken of the result and this represents the variation in time of the $CO_2$ concentration in each breathing phase.

That is, for the gas mixture, the above equation reads:

$$I = I_o \cdot e^{(-(k_{CO_2} \cdot c_{CO_2} + k_{N_2O} \cdot c_{N_2O} + \ldots) \cdot 1)}$$

Since in the inspiration phase, $c_{CO_2}$ is approximately zero and $c_{N_2O}$ in the inspiration and expiration phases differ only insignificantly from each other, the results are, after division $$\frac{I \text{ expir.}}{I \text{ inspir.}} = e^{(-k_{CO_2} \cdot c_{CO_2} \cdot 1)}$$

and after logarithmation $$l_n \frac{I \text{ expir.}}{I \text{ inspir.}} - k_{CO_2} \cdot c_{CO_2} \cdot 1$$

In consequence, the output of the computing unit is $$l_n \frac{I \text{ expir.}}{I \text{ inspir.}} \triangleq c_{CO_2}$$

Therefore, variations of $I_o$ caused, for example, by aging or misadjustment of the optic, cannot lead to a measuring error. For the same reason, the presence of $N_2O$ or other gases, the concentration of which changes only to an insignificant extent during the inspiration and expiration phases, does not affect the measurement either.

To determine the value of the $CO_2$ concentration at the end of the expiration phase, in the computing unit 6, the quotient between the maximum 12 and minimum 13 values is alternately formed and the logarithm thereof is subsequently taken.

Due to the physical and physiological interrelationship, the maximum value 12 of the $CO_2$ concentration is identical with the value at the end of the expiration phase.

It is advisable to provide for an indication only of this value 12 corresponding to the end of the expiration phase. This is done in the indicating unit 7b. The $CO_2$ value variable in time may be supplied to a terminal 7a to which a stenotype machine or an oscillograph may be connected.

While a specific embodiment of the invention has been shown and described in detail to illustrate the application of the principles of the invention, it will be understood that the invention may be embodied otherwise without departing from such principles.

What is claimed is:

1. A gas measuring device comprising an annular mounting device having an opening therethrough, a respiratory gas tube extending through the opening and being held in said mounting device, a luminous source in said mounting device arranged on one side of said tube, an interference filter mounted on said mounting device and arranged in the path of rays from said luminous source and in the path of said tube, lens means on said mounting device for directing the rays through the tube and the gases therein, and a photodetector mounted on said mounting device on the other side of said tube from said luminous source.

2. A gas measuring device, according to claim 1, including a heater associated with said mounting means for heating said tube to prevent condensation.

3. A gas measuring device, according to claim 1, including a light modulator provided between said luminous source and said interference filter.

* * * * *